US006997946B2

(12) United States Patent
Girton et al.

(10) Patent No.: US 6,997,946 B2
(45) Date of Patent: Feb. 14, 2006

(54) EXPANDABLE STENTS

(75) Inventors: Timothy Girton, Edina, MN (US); Timothy Ley, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/306,518

(22) Filed: Nov. 27, 2002

(65) Prior Publication Data

US 2004/0102833 A1    May 27, 2004

(51) Int. Cl.
*A61F 2/06* (2006.01)

(52) U.S. Cl. .................................................... 623/1.15
(58) Field of Classification Search ............... 623/1.15, 623/1.11–1.14, 1.16–1.21; 606/108, 194
See application file for complete search history.

(56) References Cited

U.S. PATENT DOCUMENTS

| | | | |
|---|---|---|---|
| 4,950,227 A | 8/1990 | Savin et al. .................... 604/8 |
| 5,156,785 A | 10/1992 | Zdrahala ..................... 264/108 |
| 5,158,548 A | 10/1992 | Lau et al. ..................... 604/96 |
| 5,344,426 A | 9/1994 | Lau et al. .................... 606/198 |
| 5,421,955 A | 6/1995 | Lau et al. ..................... 216/48 |
| 5,514,154 A | 5/1996 | Lau et al. .................... 606/195 |
| 5,546,646 A | 8/1996 | Williams et al. .......... 29/407.08 |
| 5,603,721 A | 2/1997 | Lau et al. .................... 606/195 |
| 5,728,158 A | 3/1998 | Lau et al. ..................... 623/12 |
| 5,733,303 A | 3/1998 | Israel .......................... 606/198 |
| 5,735,893 A | 4/1998 | Lau et al. ....................... 623/1 |
| 5,738,674 A | 4/1998 | Williams et al. ................ 606/1 |
| 5,766,238 A | 6/1998 | Lau et al. ....................... 623/1 |
| 5,782,855 A | 7/1998 | Lau et al. .................... 606/194 |
| 6,056,776 A | 5/2000 | Lau et al. ................... 623/1.16 |
| 6,066,167 A | 5/2000 | Lau et al. ....................... 623/1 |
| 6,066,168 A | 5/2000 | Lau et al. ................... 623/1.16 |
| 6,309,412 B1 | 10/2001 | Lau et al. ................... 623/1.11 |
| 6,312,459 B1 * | 11/2001 | Huang et al. ............... 623/1.15 |
| 6,325,824 B1 * | 12/2001 | Limon ......................... 623/1.2 |
| 6,565,597 B1 | 5/2003 | Fearnot et al. ............. 623/1.14 |
| 2003/0139799 A1 | 7/2003 | Ley et al. ................... 623/1.15 |

FOREIGN PATENT DOCUMENTS

| | | |
|---|---|---|
| WO | 99/16418 | 4/1999 |
| WO | 02/13725 | 2/2002 |
| WO | 02/91958 | 11/2002 |

* cited by examiner

*Primary Examiner*—Alvin J. Stewart
(74) *Attorney, Agent, or Firm*—Vidas, Arrett & Steinkraus (57) ABSTRACT

An intraluminal medical device having a flowpath therethrough, the device including a plurality of substantially cylindrical serpentine shaped segments which define a generally tubular body, each serpentine segment having a plurality of struts interconnected by alternating end portions, segments which are adjacent one another connected one to the other. The medical device has a pre-crimped diameter and crimped diameter and is constructed and arranged such that as the cylindrical shaped segments are crimped from the pre-crimped diameter to the crimped diameter at least some of the end portions project into the flowpath.

22 Claims, 11 Drawing Sheets

EXPANDABLE STENTS

FIELD OF THE INVENTION

The present invention relates to endoprosthesis devices adapted for implantation into a body lumen such as a blood vessel to maintain the patency thereof

BACKGROUND OF THE INVENTION

Intraluminal medical devices, for example, stents, are employed in a number of medical procedures and their structure and function are well known. Stents are typically cylindrical or tubular radially expandable prostheses introduced via a catheter assembly into a lumen of a body vessel in a configuration having a generally reduced diameter, i.e. in a crimped or unexpanded state, and are then expanded to the diameter of the vessel. In their expanded state, stents support or reinforce sections of vessel walls, for example a blood vessel, which have collapsed, are partially occluded, blocked, weakened, or dilated, and maintain them in an open unobstructed state. They have also been implanted in the urinary tract, in bile ducts, in the alimentary tract, in the tracheobronchial tree, in cerebral aqueducts, in the genitourinary system, in the prostatic urethra, in fallopian tubes, as well as other regions of the body. Stents are advantageous because they can reduce the likelihood of restenosis, and because the patency of the blood vessel is maintained immediately after the intravascular treatment.

Stents are available in self-expanding and in mechanically expandable versions which employ a dilatation balloon for expansion. Both versions are well known and widely available in a variety of designs and configurations, and are made from a variety of materials including plastics and metals with metals being more typically used. Hybrid stents which have self-expanding and mechanically expandable characteristics are also known.

Various methods are employed for delivery and implantation of a stent. For instance, a self-expanding stent may be positioned at the distal end of a catheter around a core lumen. Self-expanding stents are typically held in an unexpanded state during delivery using a variety of methods including sheaths or sleeves which cover all or a portion of the stent. When the stent is in its desired location of the targeted vessel the sheath or sleeve is retracted to expose the stent which then self-expands upon retraction.

Another method includes mounting a mechanically expandable stent on an expandable member, such as a dilatation balloon provided on the distal end of an intravascular catheter, advancing the catheter through a patient's vasculature to the desired location within the patient's body lumen, and inflating the balloon on the catheter to expand the stent into a permanent expanded condition. One method of inflating the balloon includes the use of inflation fluid. The expandable member is then deflated and the catheter removed from the body lumen, leaving the stent in the vessel to hold the vessel open.

The advancement of the stent through a patient's vasculature can involve traversing sharp bends and other obstacles which may require the stent to be highly flexible and trackable.

SUMMARY OF THE INVENTION

The present invention provides a tubular, flexible, expandable intraluminal device generally referred to as a stent which has improved retention on the surface of a dilatation member, while maintaining radial strength in an expanded condition to maintain the patency of a body lumen such as an artery when implanted therein.

In one embodiment, the present invention relates to an intraluminal medical device having a flowpath therethrough. The device includes a plurality of substantially cylindrical serpentine shaped segments which define a generally tubular body, each serpentine segment having a plurality of interconnected struts interconnected by alternating first and second end portions, the segments which are adjacent one another connected one to the other. Further, the medical device has a pre-crimped diameter and crimped diameter and is constructed and arranged such that as the cylindrical shaped segments are crimped from the pre-crimped diameter to the crimped diameter at least some of the end portions project into the delivery device. The projection of the end portions inwardly provides for improved securement to the delivery device prior to deployment at the desired location in the patient.

The interconnected struts may be parallel or non-parallel.

In some embodiments, the end portions are substantially elliptical and the struts are substantially parallel forming substantially u-shaped members.

In some embodiments, the serpentine segments may be connected by connecting members of any configuration including curved, bent, linear, curvilinear, straight and so forth. In one particular embodiment, the connecting members are straight.

The present invention further relates to the intraluminal medical devices in combination with a catheter assembly which may further include an inflation member.

The present invention further relates to a method of making the intraluminal medical devices described herein.

BRIEF DESCRIPTION OF THE FIGURES

FIG. 6b is a schematic representation of a tubular stent according to the present invention illustrating a crimped diameter relative to the pre-crimped diameter as illustrated in FIG. 6a.

FIG. 7b shows a three-dimensional view of the tubular stent shown in FIG. 8a.

FIG. 8b shows a three-dimensional view of an alternative embodiment of the tubular stent of the present invention having the stent pattern of FIG. 8a.

DETAILED DESCRIPTIONS OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

The radially expandable stents of the present invention are designed for relative flexibility along the longitudinal axis of the stent to facilitate delivery through tortuous body lumens, but exhibit radial strength in an expanded state to maintain the patency of a body lumen such as an artery when implanted therein.

The radially expandable stents of the present invention may have a first pre-crimped or manufactured diameter, a second crimped diameter, and a third expanded diameter wherein the third diameter desirably exceeds the first diameter.

In some embodiments, the present invention is directed to mechanically expandable stents formed with a pattern as described below, such pattern which is adapted for radial expansion from a first unexpanded or pre-crimped diameter to a second crimped diameter, and then to a third expanded diameter which approximates the inner diameter of the body lumen into which the stent is intended for implantation. The first pre-crimped diameter and third expanded diameter may or may not be similar. As noted above, the stents also have a second diameter referred to generally herein as the crimped diameter. The stents of the present invention desirably have a first unexpanded or pre-crimped diameter which is significantly larger than the second crimped diameter. The pre-crimped diameter may be substantially the same as the tubing size from which the stent is cut. Thus, the pre-crimped diameter may also be referred to as the diameter of the tubing as manufactured.

One method of expanding a mechanically expandable stent is through the use of an inflation member, such as a dilatation balloon.

The stents may be further designed so as to have flexible portions which deform during bending and portions which provide improved radiopacity and radial strength which remain largely undeformed during bending.

Figure 1:
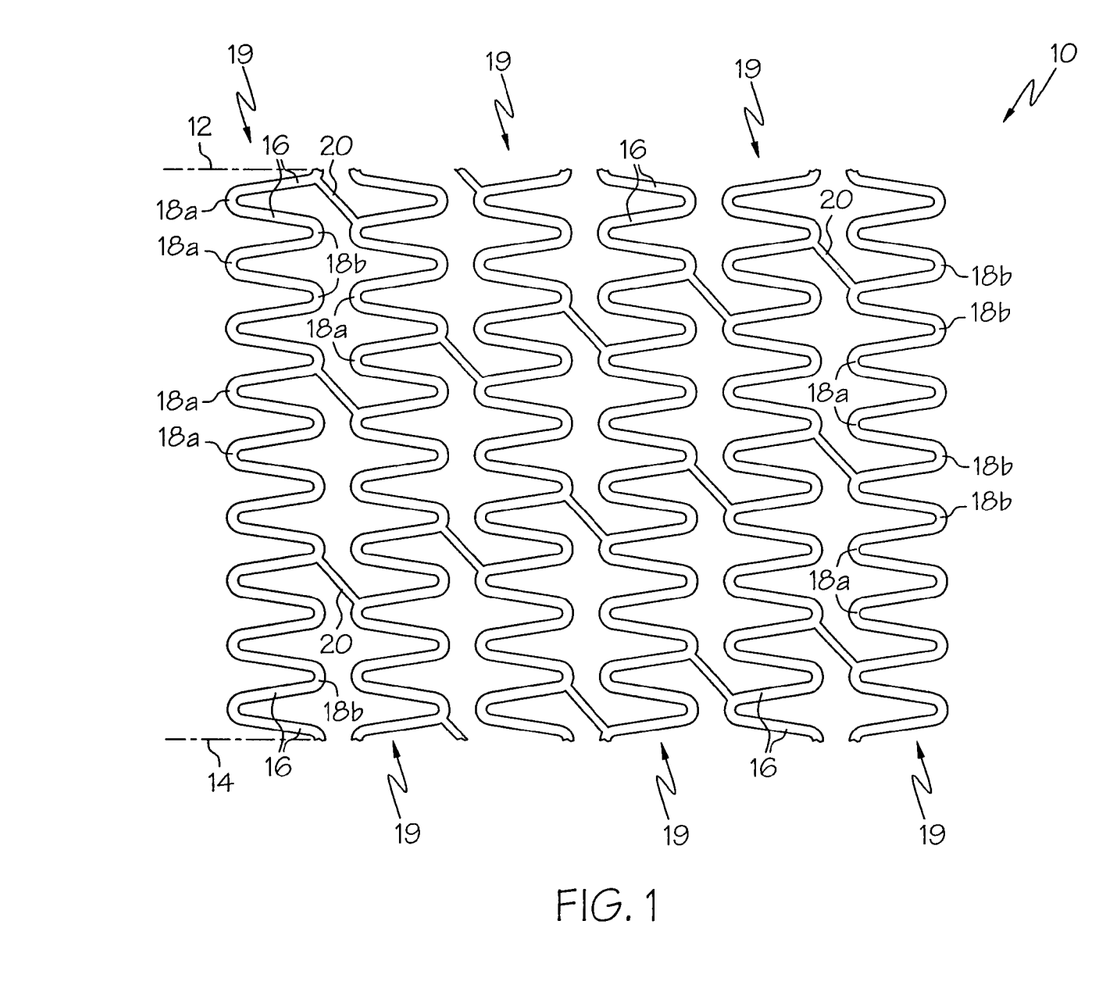
FIG. 1 is a partial flat view of a stent according to the present invention in an unexpanded state.

Turning now to the figures, FIG. 1 shows a fragmentary flat view of one embodiment of an unexpanded stent according to the present invention exhibiting a plurality of adjacent segments 19, each of which is formed in an undulating flexible pattern of non-parallel struts 16. The struts may also be parallel. Pairs of struts are interconnected at alternating end portions 18a and 18b. As seen in FIG. 1, the interconnecting end portions 18b of one segment are positioned opposite interconnecting end portions 18a of adjacent segments. The end portions shown are generally elliptical resulting in substantially U-shaped members formed by adjacent non-parallel struts. However, such end portions may be rounded, squared, pointed, and so forth. Any configuration of the end portions is acceptable providing that it results in a serpentine or undulating pattern.

The stents of the present invention, in general, may be described as tubular, radially expandable structures which include a plurality of cylindrical shaped open segments 19 aligned on a common longitudinal axis to define a generally tubular stent body. Each segment 19 may be defined by a member formed in an undulating flexible pattern of interconnected struts 16 with pairs thereof having alternating interconnecting end portions 18a, 18b to define the periphery of the expandable stent segment 19. The connected end portions 18a, 18b of paired struts 16 in each segment 19, before the stent is expanded, are optionally positioned substantially opposite to connected end portions 18a, 18b of paired struts 16 in adjacent segments 19 and are 180° out of phase with one another. In other embodiments, they may be in phase with one another or may have any other phase relationship.

The segments 19 are interconnected by a plurality of interconnecting elements 20 extending from some of the connected end portions 18a, 18b on one segment 19 to some of the connected end portions 18a, 18b on adjacent segments 19. In the particular embodiment shown in FIG. 1, the connecting elements 20 extend angularly from connecting end portion 18a, 18b of one segment to connecting end portion 18a, 18b of an adjacent segment 19, not to an opposite connecting end portion 18a, 18b on an adjacent segment 19, whereby upon expansion of the stent 10 the adjacent segments 19 are displaced relative to each other about the periphery of the stent body to accommodate flexing of the stent 10 within paired struts 16 without interference between adjacent segments 19. However, it is important to note that while the connecting elements in this particular embodiment are angular, the connectors may be straight, curvilinear, curved and so forth including s-shaped connectors, u-shaped connectors, v-shaped connectors, and so forth. The present invention is not intended to be limited to any particular type of connector and flexing may occur in the connectors, in the segment or both.

Figure 2:
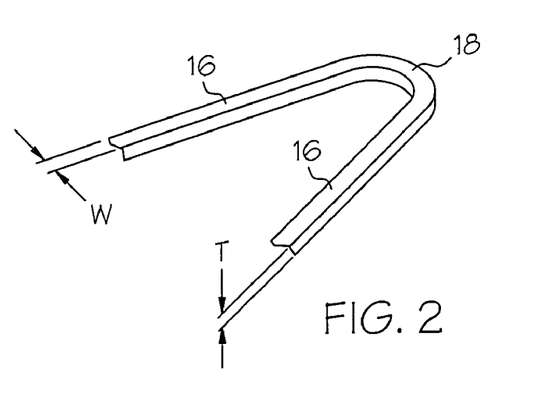
FIG. 2 illustrates a pair of parallel struts connected by an end portion in a pre-crimped state.

In the particular embodiment shown in FIG. 2, the struts 16 and substantially elliptical end portions 18 form what may be referred to as a substantially U-shaped member shown in its pre-crimped state in FIG. 2. Of course, depending on the shape of the end portions 18a, 18b, the shape of the member will also vary and the present invention is not intended to be limited to any particular shaped end portion.

Figure 3:
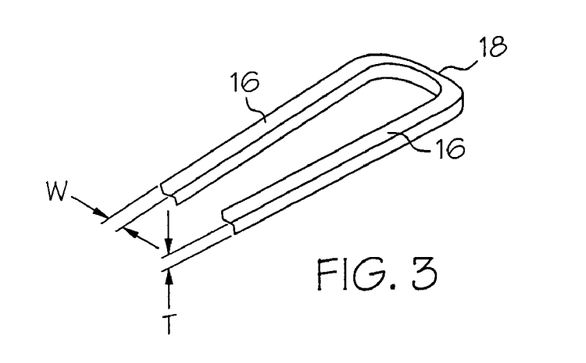
FIG. 3 illustrates the same pair of struts as shown in FIG. 2 in a crimped state.

The U-shaped member of FIG. 2, for example, is shown in its crimped state in FIG. 3. The end portions 18 are shown projecting inwardly according to the present invention. Without being bound by theory, the result of the projection of the end portions inwardly during crimping provides enhanced securement of the stent to an inflation member on a catheter delivery device for example, and also may result in improved tracking of the device through the vasculature.

Figure 4:
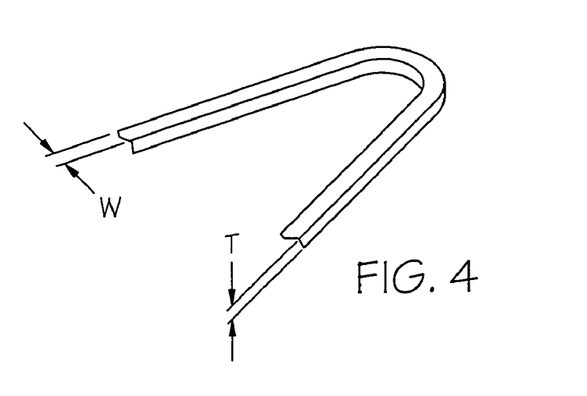
FIG. 4 illustrates the same pair of struts as shown in FIGS. 2 and 3 in an expanded state.

The U-shaped member is further shown in an expanded state in FIG. 4. The ends 19 are shown having little projection either inwardly or outwardly in the expanded state.

Suitably, the struts 16 of the intraluminal devices of the present invention have a strut width W which is not less than the strut thickness T shown in FIGS. 2–4.

Figures 5A, 5B:
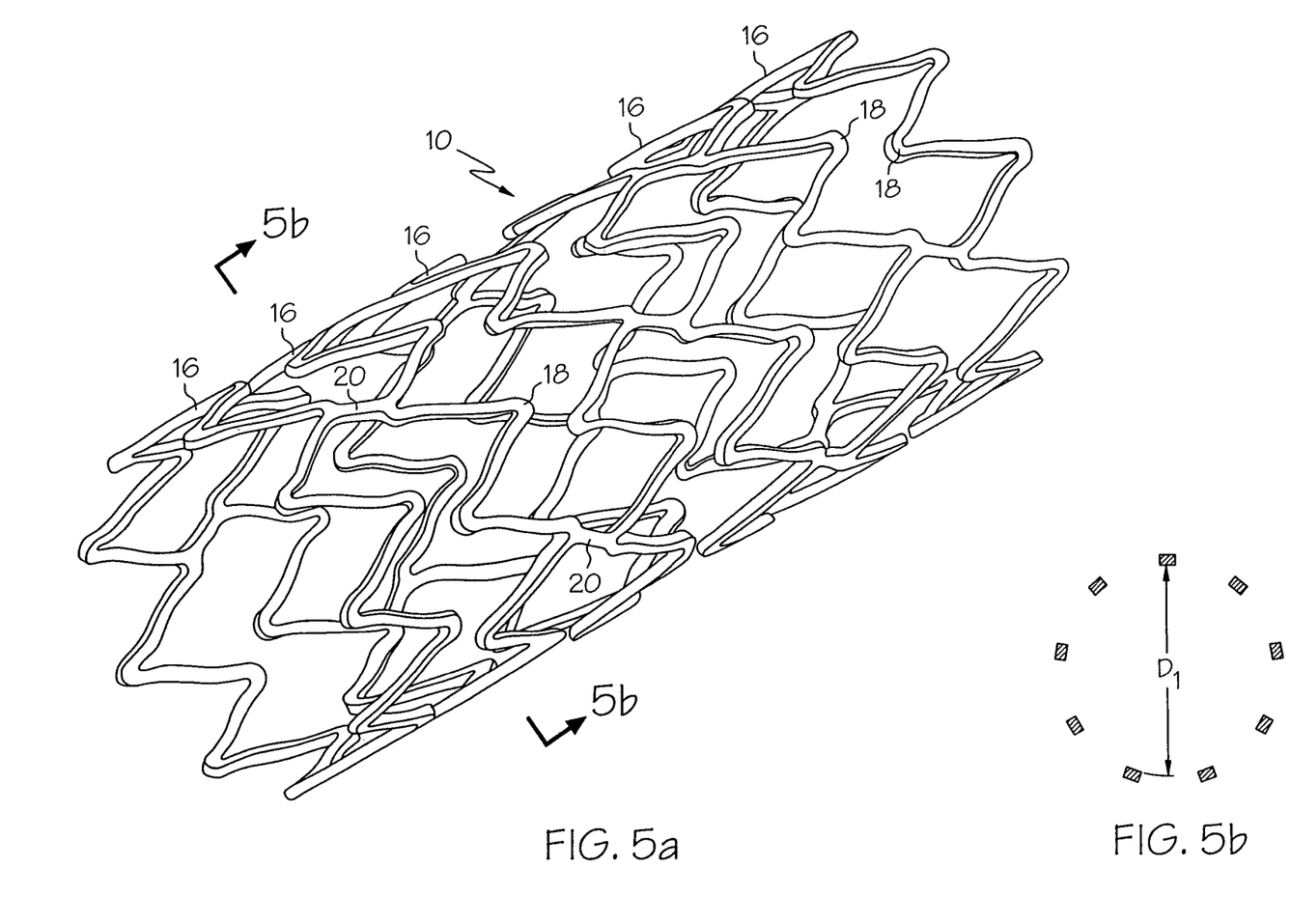
FIG. 5a shows a three-dimensional view of one embodiment of a tubular stent in a pre-crimped state.
FIG. 5b is a representation of the precrimped diameter of the tubular stent of FIG. 5a taken at section 5b.
Figures 5C, 5D:
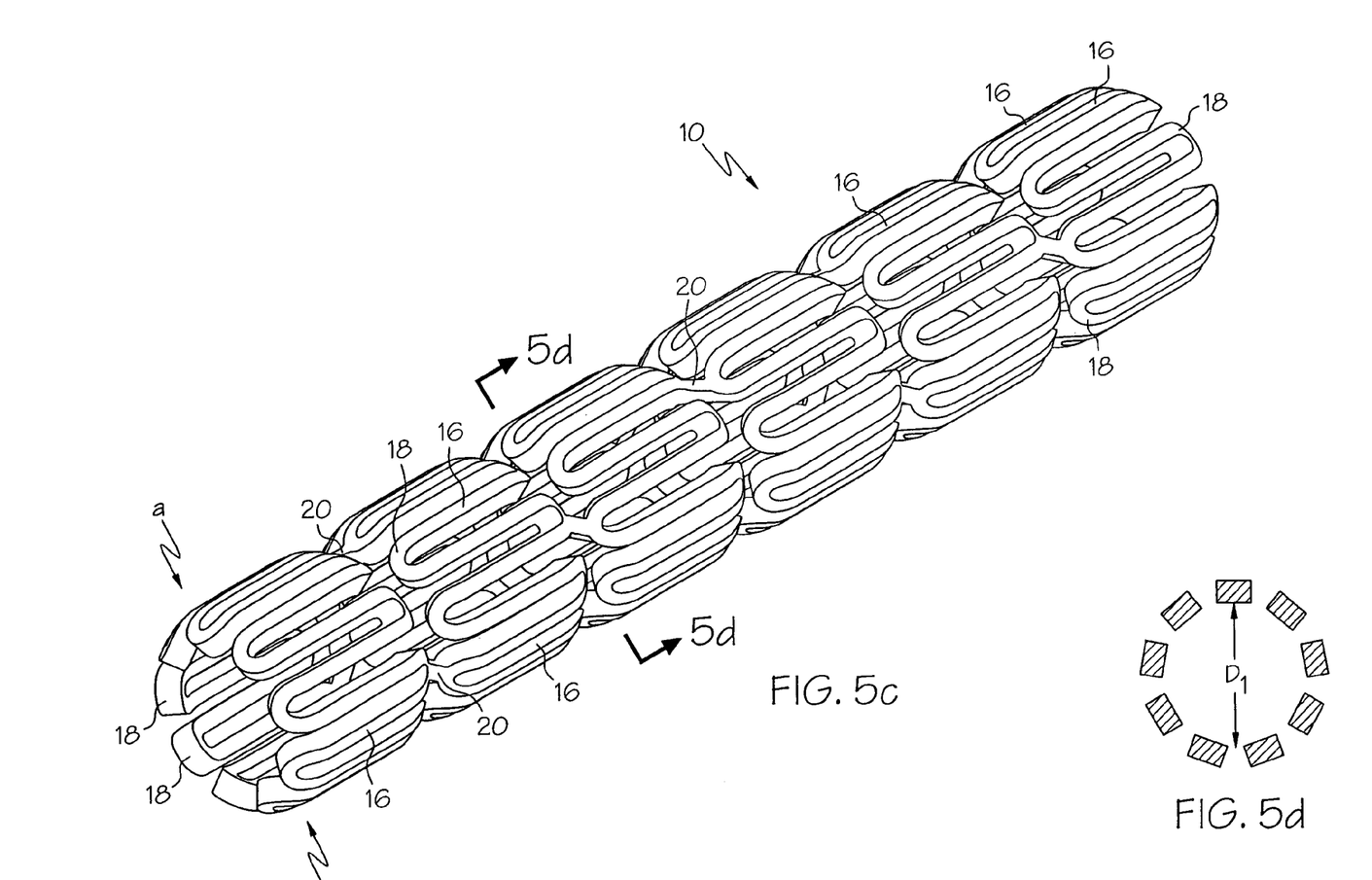
FIG. 5c shows the same stent as FIG. 5a in a crimped state.
FIG. 5d is a representation of the crimped diameter of the tubular stent of FIG. 5c taken at section 5d.

FIG. 5a illustrates generally at 10, a tubular, expandable stent of the present invention in its pre-crimped state. The diameter D1 of the stent in its pre-crimped state is taken at the proximal end of the stent and is noted as section 5b and is shown in FIG. 5b. The diameter of the stent in the pre-crimped state is substantially equal to the diameter of the tubing from which the stent is cut and may typically be in the range of about 0.04" (about 1.0 mm) to as high as about 0.4" (about 10 mm) or higher. The range of tubing size employed may vary depending on the intended use of the stent. FIG. 5c shows the stent of FIG. 5a in a crimped state. The stent in its crimped stated has a diameter D2. The stent is typically crimped to a diameter of about 0.025" (about 0.6 mm) to about 0.08" (about 2 mm), and more typically about 0.04" (about 1 mm) to about 0.05" (about 1.3 mm). Again, this size may be dictated by the intended use of the stent. The diameter D2 of the stent in the crimped state is shown in FIG. 5d.

Figure 6A:
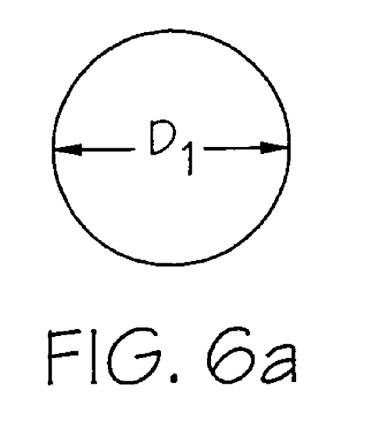
FIG. 6a is a schematic representation of a tubular stent according to the present invention illustrating a pre-crimped diameter.
Figure 6B:
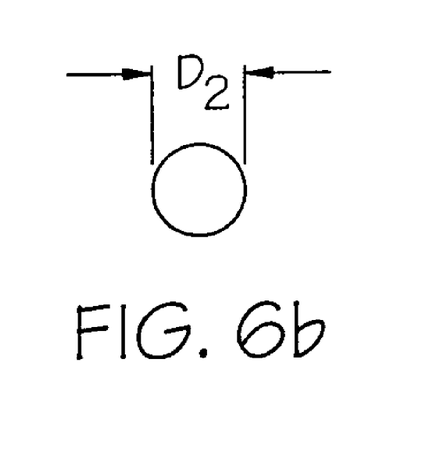

Typically, the diameter D1 of a stent in the pre-crimped state is similar to the diameter D2 of the stent in the crimped state in contrast to the present invention in which the diameter D1 of the stent in the pre-crimped state is significantly larger than the diameter D2 of the stent in the crimped state. FIGS. 6a and 6b, expanded views, illustrate an embodiment of the invention in which the stent is crimped from a pre-crimped diameter D1 to a crimped diameter D2. The pre-crimped diameter D1 is approximately four times that of the crimped diameter D2.

In an expanded state, a stent may range from about 2 mm to about 30 mm (about 0.08" to about 1.2").

Figure 7A:
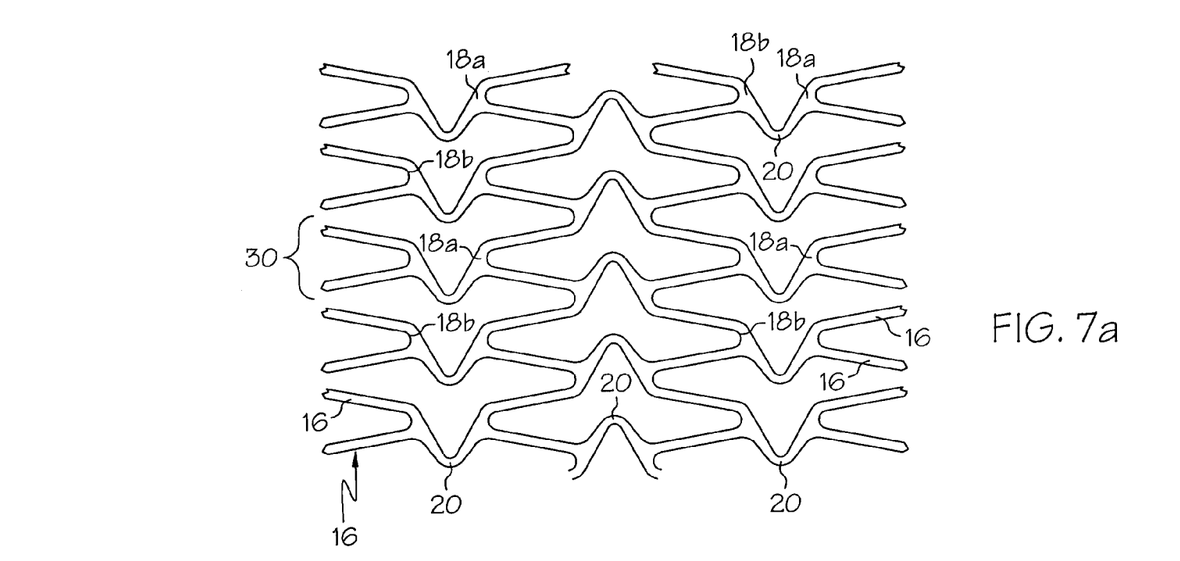
FIG. 7a is a partial flat view of an embodiment of a stent of the present invention in a pre-crimped state.

FIG. 7a shows a partial flat view of an alternative embodiment of a stent of the present invention in a pre-crimped state in which connectors 20, rather than being angular as shown in one embodiment above, are curved. The curvature of such connectors 20 may be varied. Connectors 20 are also shown between every adjacent end portion 18a, 18b between strut pairs 16. In the embodiment shown in FIG. 1, for example, there are fewer connectors 20 between pairs of struts 16 with one connector 20 for every three pairs of struts 16.

The strut pairs, shown as being substantially parallel, are joined by elliptical end portions 18a, 18b as shown in the embodiment in FIG. 1 forming substantially u-shaped members.

Figure 7B:
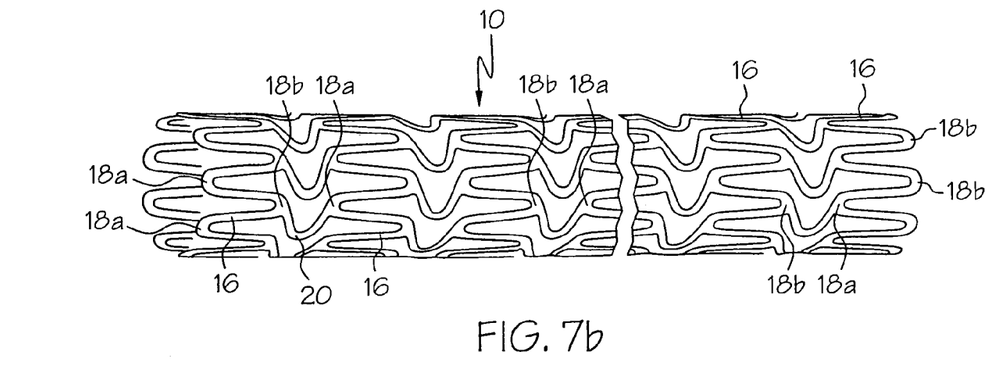

FIG. 7b illustrates the same stent as shown in FIG. 7a but in the tubular form. The stent may be formed by etching the pattern in a flat sheet and then rolling the sheet and sealing the edges together such as by welding in the case of a metal, or the stent pattern may be cut from a hollow tubular member. The stent may be formed from multiple sheets or multiple tubular members, as well as from multiple materials. As used herein, the term "multiple" shall be used to refer to two or more.

Figure 7C:
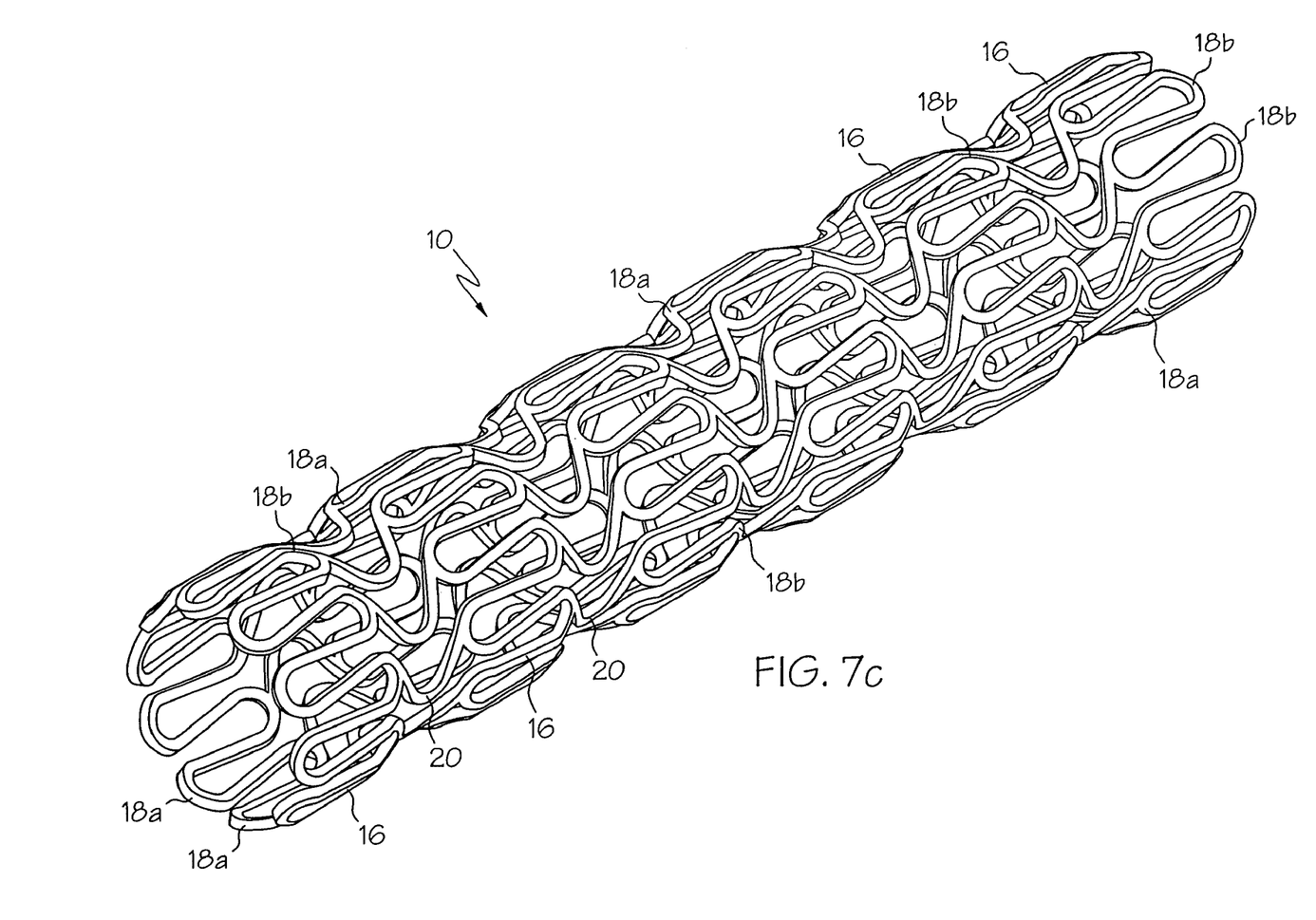
FIG. 7c illustrates the same stent as shown in FIGS. 7a and 7b in a crimped state.

FIG. 7c illustrates the same stent as shown in FIGS. 7a and 7b in a crimped state. The end portions 18a, 18b of the u-shaped members project inwardly as shown in FIG. 7c. The diameter of the stent in a pre-crimped state is significantly larger than the diameter of the stent in the crimped state. FIGS. 7b and 7c are not shown dimensionally accurate to one another.

Figure 7D:
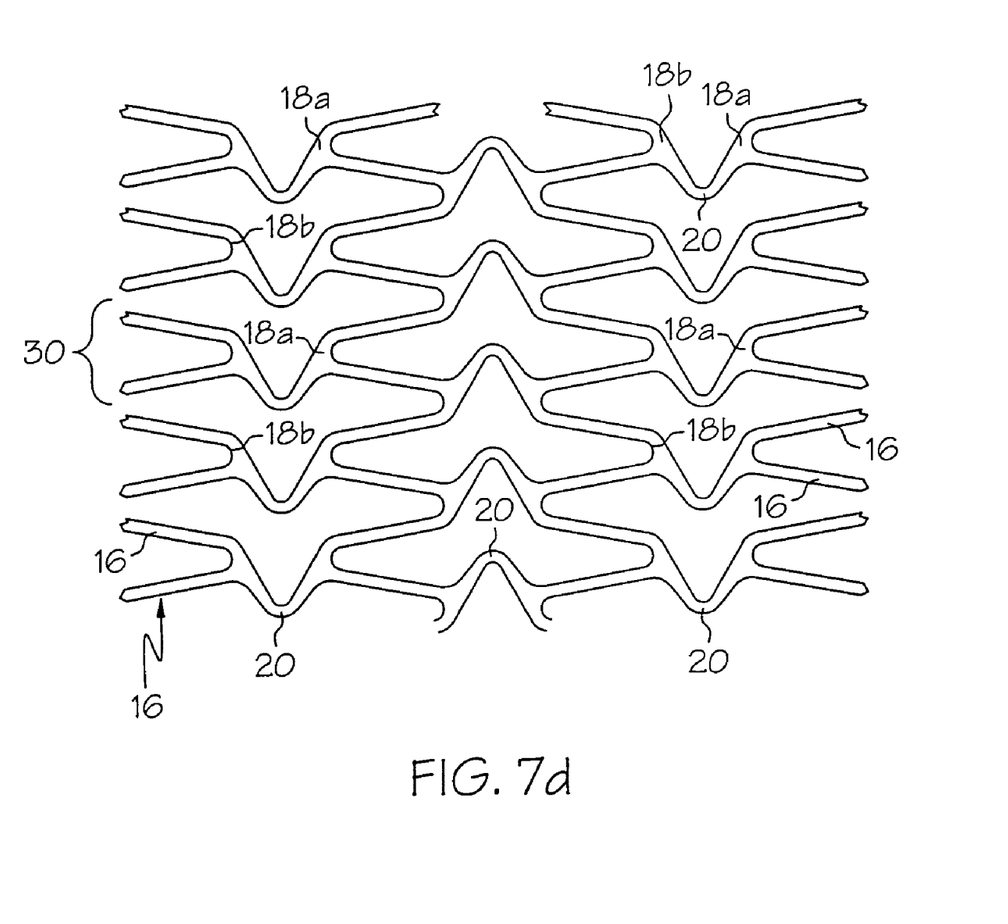
FIG. 7d shows a partial flat view of the stent of FIGS. 7a–7c in a pre-crimped state.

FIG. 7d shows a partial flat view of the stent in an expanded state. In the expanded state, the end portions 18a, 18b of the u-shaped members do not project outwardly to any significant extent.

Figure 8A:
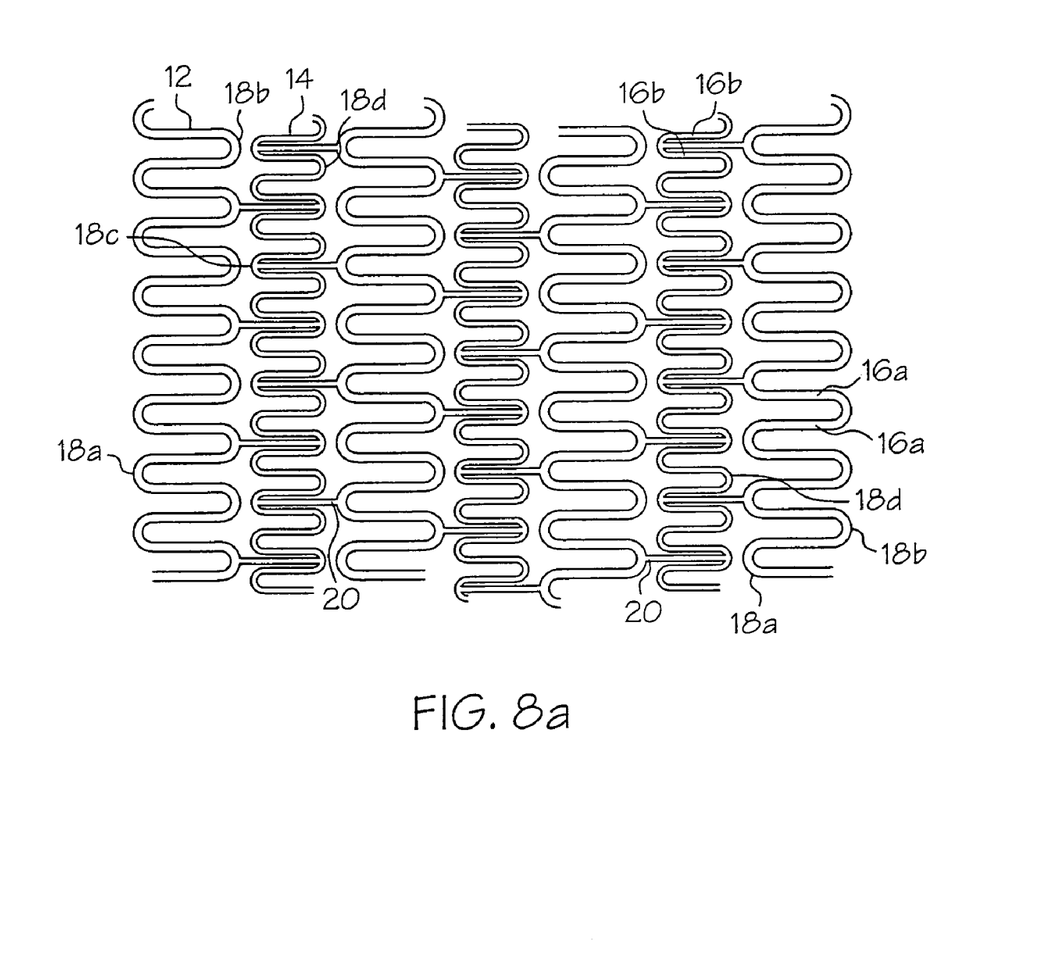
FIG. 8a shows a partial flat view of an embodiment of the stent of the present invention in a pre-crimped state.

FIG. 8a shows a partial flat view of an alternative embodiment of a stent of the present invention in a pre-crimped state in which connectors 20 are straight.

Figure 8B:
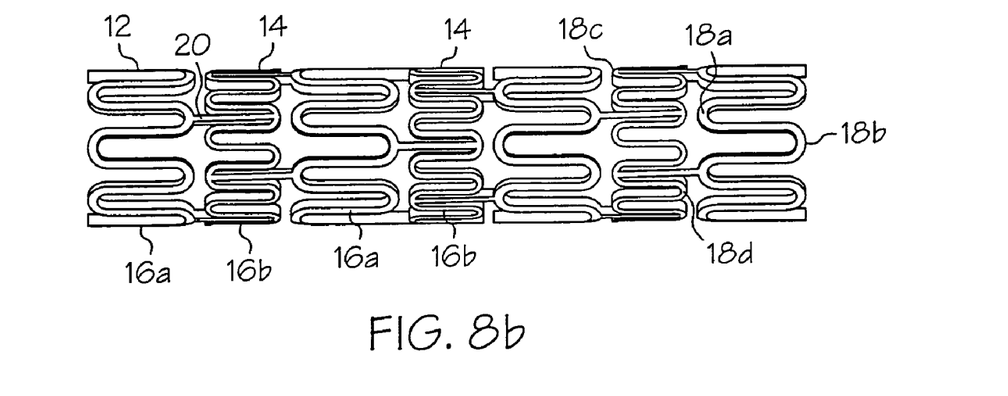

FIG. 8b shows a three dimensional view of the stent of FIG. 8a in its tubular form. In this embodiment, a first serpentine portion 12 eight peaks and eight troughs also referred to herein as end portions 18a, 18b per serpentine portion. There are four connectors 20 per serpentine band. Every second peak has a connector 20 extending therefrom.

A second serpentine portion 14 has twelve peaks and twelve troughs per serpentine portion also referred to herein as end portions 18c, 18d. Every third trough has a connector 20 extending therefrom. The ratio of end portions in the first serpentine band to end portions in the second serpentine band is thus 2:3. End portions 18a, 18b are elliptical and form U-shaped members between adjacent struts 16a of the first serpentine portions 12. Struts 16a are longer than struts 16b of the second serpentine portions 14 which are also connected by elliptical shaped end portions 18c, 18d.

In this embodiment as well as the other embodiments disclosed herein, the stent may be formed by laser cutting a tube of stainless steel, or any other suitable stent material, and polished to smooth and round the edge surfaces. However, such a pattern may also be cut from a single flat sheet of metal such as stainless steel, and then rolling the sheet and sealing the edges together such as by welding in the case of a metal, or the stent pattern may be cut from a hollow tubular member. Furthermore, the stent may be formed from more than one flat sheet or from one tubular member. The stent may be formed using multiple materials as well.

Figure 8C:
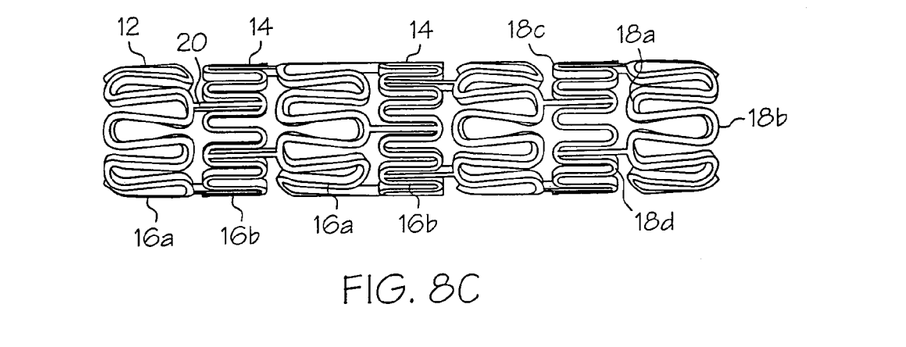
FIG. 8c shows a three-dimensional view of the same stent shown in FIGS. 8a and 8b in a crimped state.

FIG. 8c illustrates the same stent as shown in FIGS. 8a and 8b in a crimped state. At least some of the end portions, 18a, 18b, 18c, 18d of the u-shaped members project inwardly as shown in FIG. 8c. The stent has first serpentine portions 12 which have struts 16a longer than struts 16b of second serpentine portions 14. The end portions 18a, 18b of first serpentine portions 12 are shown projecting inwardly. The end portions 18c, 18d of second serpentine portions 14 are shown in this embodiment as not projecting inwardly. However, in an alternate embodiment, end portions 18c, 18d of second serpentine portions 14 could also project inwardly.

The diameter of the stent shown in FIGS. 8a–8c in a pre-crimped state is larger than the diameter of the stent in the crimped state. It is important to note that the stents, and thus the diameters, are not drawn to scale. The diameter should be reduced by a factor of at least about 2 from the pre-crimped state to the crimped state. FIGS. 8b and 8c are not shown dimensionally accurate to one another and thus are not representative of the relative diameters of the stent as shown in FIG. 8b to that same stent in crimped form shown in FIG. 8c.

Figure 10:
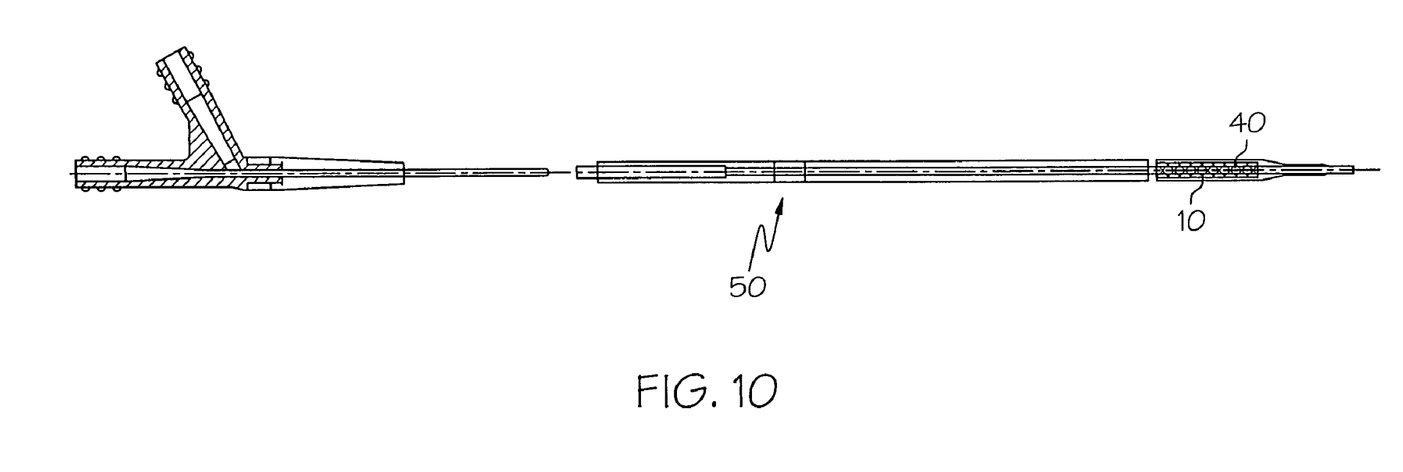
FIG. 10 shows a stent mounted on the distal end of a catheter delivery device.

FIG. 10 shows the same stent as in FIG. 8c in its crimped state and mounted on a dilatation member 40.

Other suitable stent patterns for use in the present invention are found, for example, in U.S. Pat. No. 5,733,303 incorporated by reference herein.

The stents of the present invention may be manufactured from any materials known in the art for use in forming such members, and suitably the tubular members may be made of a biocompatible material. Examples include, but are not limited to, the shape memory materials, noble metals, transition metals, any alloys of the shape memory materials, noble metals, transition metals, polymeric materials, and so forth.

Suitably, the stent may be manufactured of stainless steel alloys which include, but are not limited to, Special Chemistry of type 316L SS per ASTM F138-92 or ASTM F139-92 grade 2 and Special Chemistry of type 316L per ASTM F138-92 or ASTM F139-92 and so forth.

Other metals suitable for formation of the inventive stents of the present invention include, but are not limited to the more radiopaque metals including the noble metals gold and platinum, and tantalum; iridium, palladium, tungsten, titanium, chromium, cobalt, molybdenum, nickel, silver, copper, zinc, and so forth, and alloys thereof.

Specific examples of alloys useful for manufacture of the inventive stents herein include, but are not limited to, nickel-titanium, cobalt-chromium, cobalt-chromium-molybdenum, and so forth.

The above materials are known to those of skill in the art and those listed are intended for exemplary purposes only. This list is by no means exhaustive of the types of materials which may be employed in the manufacture of the stents of the present invention.

The stent may be formed according to any method known in the art including etching a pattern and then rolling the sheet and sealing the edges together such as by welding, for example, or the stent may be cut from a hollow tube. If a flat metal sheet is employed, the etched pattern is then rolled into a tube and the tube is optionally welded or the like.

Figure 9:
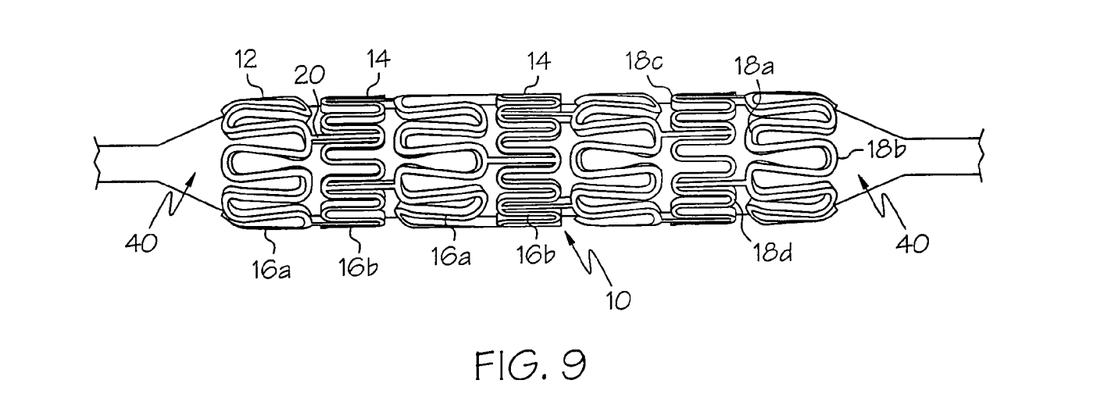
FIG. 9 shows a stent in a crimped state mounted on a dilatation member.

The stents of the present invention in combination with the inflation members may be further mounted on the distal end of a stent delivery catheter which is then passed through the body lumen to the site of implantation. The stent is mounted on the balloon catheter by crimping it onto the catheter employing methods known in the art. FIG. 9 illustrates a stent 10 of the present invention shown crimped to a dilatation member, in this embodiment, a catheter balloon 40 of a delivery catheter shown generally at 50.

The catheter delivery device shown in FIG. 10 is intended for illustrative purposes only. Catheter delivery devices useful for delivery of a medical device of the type described herein are well known to those of ordinary skill in the art and as such any suitable delivery catheter may be employed herein.

The stent and the inflation member are typically compressed or crimped onto the catheter structure for delivery to the implantation site where the inflation member is inflated typically with an inflation fluid thus expanding the stent. Crimping devices are well known in the art and any suitable crimping device may be employed. The inflation member is then deflated and the catheter assembly removed from the body lumen leaving the stent behind.

The above disclosure is intended for illustrative purposes only and is not exhaustive. The embodiments described therein will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

We claim:

1. An intraluminal medical device having a central longitudinal axis having a pre-crimped state, a crimped state, and an expanded state, the device comprising:
   a plurality of substantially cylindrical serpentine shaped segments which define a generally tubular body, each serpentine segment having a plurality of stints interconnected by alternating end portions, segments which are adjacent one another connected one to the other;
   the medical device in a crimped state having at least some end portions which project inward into the central longitudinal axis, the end portions which extend into the central longitudinal axis being closer to the central longitudinal axis than the struts which they connect, the end portions equidistant from the central longitudinal axis.

2. The intraluminal medical device of claim 1 wherein said intraluminal medical device is a stent.

3. The intraluminal medical device of claim 2 wherein the pre-crimped diameter of the stent is about 0.1" or greater.

4. The intraluminal medical device of claim 2 wherein the pre-crimped diameter of the stent is about 0.15" or greater.

5. The intraluminal medical device of claim 2 a wherein the pre-crimped diameter of to stent is about 0.05" to about 0.35".

6. The intraluminal medical device of claim 2 wherein to pre-crimped diameter of the stent is about 0.1" to about 0.25".

7. The intraluminal medical device of claim 2 wherein the crimped diameter of the stent is about 0.025" to about 0.08".

8. The intraluminal medical device of claim 2 wherein the crimped diameter of the stent is about 0.04" to about 0.05".

9. The intraluminal medical device of claim 1 comprising a plurality of connecting members, each connecting member connecting cylindrical shaped segments which are adjacent one another.

10. The intraluminal medical device of claim 1 wherein the medical device is constructed and arranged such that as the cylindrical shaped segments are crimped from the pre-crimped diameter to the crimped diameter more than half of the end portions project inward.

11. The intraluminal medical device of claim 1 wherein the medical device is constructed and arranged such that as the cylindrical shaped segments are crimped from the pre-crimped diameter to the crimped diameter all of the end portions project inward.

12. The intraluminal medical device of claim 1 wherein the pre-crimped diameter is about two times the crimped diameter or greater.

13. The intraluminal medical device of claim 1 wherein the pre-crimped diameter is about four times the crimped diameter or greater.

14. The intraluminal medical device of claim 1 wherein the medical device is comprised of at least one metal, at least one plastic or composites thereof.

15. The intraluminal medical device of claim 14 wherein the metal is stainless steel.

16. The intraluminal medical device of claim 1 wherein said intraluminal medical device is mechanically expandable.

17. The intraluminal medical device of claim 1 wherein the medical device is a thin-walled tubular member.

18. The intraluminal medical device of claim 1 in combination with a catheter delivery device, the medical device disposed about a portion of the catheter delivery device.

19. The intraluminal medical device of claim 18 further including an inflation member.

20. The intraluminal medical device of claim 19 wherein said inflation member is a dilatation balloon.

21. The intraluminal medical device of claim 1 wherein the serpentine shaped segments are comprised of a plurality of interconnected struts, the struts having a minimum width equal to or greater than a maximum strut thickness.

22. The intraluminal medical device of claim 1 wherein said end portions exhibit substantially no inward projection in a pre-crimped state.

* * * * *